(12) United States Patent
Zemlan

(10) Patent No.: US 7,361,667 B2
(45) Date of Patent: Apr. 22, 2008

(54) 4',4''-SUBSTITUTED 3α-(DIPHENYLMETHOXY) TROPANE ANALOGS FOR TREATMENT OF MENTAL DISORDERS

(75) Inventor: Frank P. Zemlan, Cincinnati, OH (US)

(73) Assignee: P2D, Inc., Cincinnati, OH (US)

( * ) Notice: Subject to any disclaimer, the term of this patent is extended or adjusted under 35 U.S.C. 154(b) by 419 days.

(21) Appl. No.: 10/752,840

(22) Filed: Jan. 7, 2004

(65) Prior Publication Data
US 2004/0142962 A1 Jul. 22, 2004

Related U.S. Application Data

(60) Provisional application No. 60/438,981, filed on Jan. 9, 2003, provisional application No. 60/451,357, filed on Mar. 3, 2003.

(51) Int. Cl.
*A01N 43/42* (2006.01)
*A61K 31/44* (2006.01)
*C07D 451/02* (2006.01)

(52) U.S. Cl. ...................... 514/304; 546/124
(58) Field of Classification Search ............... 514/304; 546/124, 125
See application file for complete search history.

(56) References Cited

U.S. PATENT DOCUMENTS 3,452,029 A 6/1969 Childress et al.
5,792,775 A 8/1998 Newman et al.

OTHER PUBLICATIONS

Katz, JL et al 'Novel 3 -diphenylmethoxytropane analogs: Selective dopamine uptake inhibitors with behavioral effects distinct form those of cocaine' CA 130:217603 (1999).*
Agoston, GE et al 'A novel potoaffinity label for the dopamine transporter based on N-substituted 3 -[bis(4'-flurophenyl)methoxy]tropane' CA 128:162491 (1998).*
Zou, MF et al 'Novel tropane-based irreversible ligands for the dopamine transporter' CA 136:85971 (2001).*
Robarge, MJ et al 'Design and synthesis of [(2,3-dichlorophenyl)piperain-1-yl]alylfluorenylcarboxamides as novel ligands selective for the dopamine D3 receptor subtype' CA 135:303847 (2001).*
Jai, H et al 'QSAR study of benztropine analogs for dopamine transporter' CA 135:282655 (2001).*
Bakken, GA et al 'Classification of multidrug-resistance reversal agents using structure-based descriptors and linear discriminant analysis' CA 134:25113 (2000).*
Katz, J.L. et al., Novel 3α-Diphenylmethoxytropane Analogs: Selective Dopamine Uptake Inhibitors with Behavioral Effects Distinct from Those of Cocaine, Journal of Pharmacology and Experimental Therapeutics (Aug. 21, 1998) pp. 203-315, vol. 288, No. 1.
Bartlik, B., Kaplan, P., & Kaplan, H. S. (1995). Psychostimulants apparently reverse sexual dysfunction secondary to selective serotonin re-uptake inhibitors. *Journal of sex & marital therapy*, 21(4), 264-271.
Dorrego, M. F., Canevaro, L., Kuzis, G., Sabe, L., & Starkstein, S. E. (2002). A randomized, double-blind, crossover study of methylphenidate and lithium in adults with attention-deficit/hyperactivity disorder: preliminary findings. *The Journal of neuropsychiatry and clinical neurosciences*, 14(3), 289-295.
Federici, M., Geracitano, R., Bernardi, G., & Mercuri, N. B. (2005). Actions of methylphenidate on dopaminergic neurons of the ventral midbrain, *Biological psychiatry*, 57(4), 361-365.
Fleming, S., Delville, Y., & Schallert, T. (2005). An intermittent, controlled-rate, slow progressive degeneration model of Parkinson's disease: antiparkinson effects of Sinemet and protective effects of methylphenidate. *Behavioural brain research*, 156(2), 201-213.
Janowsky, D. S. (2003). Depression and dysphoria effects on the interpersonal perception of negative and positive moods and caring relationships: effects of antidepressants, amphetamine, and methylphenidate. *Current psychiatry reports*, 5(6), 451-459.
Jensen, P., Hinshaw, S., Swanson, J., Greenhill, L., Connors, C., Arnold, L. et al. (2001). Findings from the NIMH Multimodal Treatment Study of ADHD (MTA): implications and applications for primary care providers. *Journal of developmental and behavioral pediatrics : JDBP*, 22(1), 60-73.
Kajs-Wyllie, M. (2002). Ritalin revisited: does it really help in neurological injury? *The Journal of neuroscience nursing : journal of the American Association of Neuroscience Nurses*, 34(6), 303-313.
Robinson, M., Anastasio, G., Little, J., Sigmon, J. L. J., Menscer, D., Pettice, Y. et al. (1995). Ritalin for nicotine withdrawal: Nesbitt's paradox revisited. *Addictive behaviors*, 20(4), 481-490.
Ritalin Hydrochloride. In Physicians' Desk Reference, Sixtieth Edition (Ed. David Sifton) 2006, p. 2254-2259, Thomson PDR, Montvale, NJ USA.
COGENTIN®, Physicians' Desk Reference (2001) 1892-1893, vol. 55, Medical Economics Company, Inc., Montvale, NJ.
Eiler et al., $D_1$ dopamine receptor regulates alcohol-motivated behaviors in the bed nucleus of the stria terminalis in alcohol-preferring (P) rats, Synapse, 48:45-56 (2003).
Tupala et al., Dopamine receptors and transporters in the brain reward circuits of type 1 and 2 alcoholics measured with human whole hemisphere autoradiography, NeuroImage 19 (2003) 145-155.

(Continued)

*Primary Examiner*—Margaret D. Seaman
*Assistant Examiner*—Niloofar Rahmani
(74) *Attorney, Agent, or Firm*—Frost Brown Todd LLC

(57) ABSTRACT

The present invention describes a method for the treatment of attention deficit hyperactivity disorder (ADHD), conduct disorder, alcohol addiction, tobacco addiction, nicotine addiction, parkinsonism including Parkinson's disease, female and male orgasmic disorders, female and male sexual arousal disorders, hypoactive sexual desire disorder, and disorders characterized by anxiety and/or depression. In this method, a therapeutically effective, nontoxic dose of a 4',4''-substituted 3α-(diphenylmethoxy) tropane analog or a pharmaceutically acceptable salt thereof is administered to the patient in need of such treatment.

12 Claims, No Drawings

OTHER PUBLICATIONS

Bahk et al., Dopamine $D_1$ and $D_2$ receptor mRNA up-regulation in the caudate-putamen and nucleus accumbens of rat brains by smoking, Progress in Neuro-Psychopharmacology & Biological Psychiatry 26 (2002) 1095-1104.

Geracioti, et al., Low CSF concentration of a dopamine metabolite in tobacco smokers, Am. J. Psychiatry 156:1, Jan. 1999.

Campiani, et al., Synthesis and pharmacological evaluation of potent and highly selectively $D_3$ receptor ligands: inhibition of cocaine-seeking behavior and the role of dopamine $D_3/D_2$ receptors, J. Med. Chem. 2003, 46, 3822-3839.

Chartoff, et al., Dopamine-dependent increases in phosphorylation of cAMP response element binding protein (CREB) during precipitated morphine withdrawal in primary cultures of rat striatum, J. Neurochem. (2003) 87, 107-118.

O'Shea and Colado, Is frequent dosing with ecstasy a risky business for dopamine-containing neurons?, Trends in Pharmacological Sciences, vol. 24, No. 6, Jun. 2003.

Earle and Stuckey, Biochemical screening in the assessment of erectile dysfunction: what tests decide future therapy?, Urology 62 (4) 727-731, 2003.

Wisor, et al., Dopaminergic role in stimulant-induced wakefulness, J. Neuroscience, Mar. 1, 2002, 21(5):17871794.

Honda, et al., Dopamine $D_3$ agonists into the substantia nigra aggravate cataplexy but do not modify sleep, NeuroReport 10, 3717-3724 (1999).

Moore, Organization of midbrain dopamine systems and the pathophysiology of Parkinson's disease, Parkinsonism and Related Disorders 9 (2003) S65-S71.

Stocchi, et al., Dual dopamine agonist treatment in Parkinson's disease, J. Neurol. (2003) 250: 822-826.

Young, et al., Dopamine transporter polymorphism associated with externalizing behavior problems in children, Am. J. of Medical Genetics (Neuropsychiatric Genetics) 114:144-149 (2002).

Seeman and Madras, Methylphenidate elevates resting dopamine which lowers the impulse-triggered release of dopamine: a hypothesis, Behavioural Brain Research 130 (2002) 79-83.

Solanto, Dopamine dysfunction in AD/HD: integrating clinical and basic neuroscience research, Behavioural Brain Research 130 (2002) 65-71.

Swanson and Volkow, Pharmacokinetic and pharmacodynamic properties of stimulants: implications for the design of new treatments for ADHD, Behavioural Brain Research 130 (2002) 73-78.

Wall, et al., Infralimbic D2 receptor influences on anxiety-like behavior and active memory/attention in CD-1 mice, Progress in Neuro-Psychopharmacology & Biological Psychiatry 27 (2003) 395-410.

Laakso, et al., Personality traits and striatal dopamine synthesis capacity in healthy subjects, Am. J. Psychiatry 2003; 160:904-910.

Lawford, et al., D2 dopamine receptor gene polymorphism: paroxetine and social functioning in posttraumatic stress disorder, European Neuropsychopharmacology 13 (2003) 313-320.

Buller, et al., Systemic apomorphine alters HPA axis responses to interleukin-1βadministration but not sound stress, Psychoneuroendocrinology 28 (2003) 715-732.

Brunswick, et al., Greater availability of brain dopamine transporters in major depression shown by [$^{99m}$Tc]TRODAT-1 SPECT imaging, Am. J. Psychiatry 2003; 160:1836-1841.

Kondo, et al., Combination of dopamine $D_2$ receptor gene polymorphisms as a possible predictor of treatment-resistance to dopamine antagonists in schizophrenic patients, Progress in Neuro-Psychopharmacology & Biological Psychiatry 27 (2003) 921-926.

* cited by examiner

4',4"-SUBSTITUTED 3α-(DIPHENYLMETHOXY) TROPANE ANALOGS FOR TREATMENT OF MENTAL DISORDERS

CROSS REFERENCE TO RELATED APPLICATIONS

The present application is based upon and claims priority from U.S. Provisional Patent Application Nos. 60/438,981, filed Jan. 9, 2003, and 60/451,357, filed Mar. 3, 2003, both of which are incorporated herein by reference.

TECHNICAL FIELD

The present invention relates to pharmaceutically active compositions consisting of 4',4"-substituted 3α-(diphenylmethoxy) tropane analogs which are used in a method for treating specific psychiatric disorders including narcolepsy, attention deficit hyperactivity disorder (ADHD), conduct disorder, alcohol addiction, tobacco addiction, nicotine addiction, inhalation disorders, Parkinsonism including Parkinson's disease, female and male orgasmic disorders, female and male sexual arousal disorders, hypoactive sexual desire disorder, and disorders characterized by anxiety and/or depression.

BACKGROUND OF THE INVENTION

The brain consists of a vast network of neurons that communicate with each other via chemical messengers. Each neuron generates neurochemicals or neurotransmitters which act at sites referred to as receptors on the cellular membranes of neurons. One group of neurotransmitters, referred to as the monoamine neurotransmitters, includes serotonin, dopamine and noradrenaline. Monoamine neurotransmitters are released into the synaptic cleft between neurons in order to stimulate post-synaptic receptor activity. The removal (or inactivation) of monoamine neurotransmitters occurs mainly by a reuptake mechanism into the pre-synaptic terminals. By inhibiting the reuptake, an enhancement of the physiological activity of monoamine transmitters occurs.

The serotonergic neural system of the brain has been shown to influence a variety of physiologic functions, and compounds having dopamine reuptake-inhibiting activity have been shown to have the ability to treat in mammals, including humans, a variety of disorders associated with this neural system, for example, eating disorders, depression, cocaine addiction, dementia of aging, memory dysfunction in aging, and attention deficit hyperactivity disorder.

However, the use of dopamine transport inhibitors to treat such conditions frequently brings along with it a number of undesirable side effects. For example, benztropine (COGENTIN™) is a high affinity dopamine transport (DAT) inhibitor that increases dopamine activity in the brain. This material has been in continuous clinical use for over forty years. Benztropine's inhibition of the dopamine transporter is responsible for its clinical effectiveness for treating idiopathic Parkinson's disease, a clinical indication for which it is FDA approved. Unfortunately, the clinical usefulness of benztropine has been severely limited by its anticholinergic properties which result from benztropine's high affinity binding to M1 cholinergic receptors. Benztropine's anticholinergic side effects, as documented in the Physician's Desk Reference, include tachycardia, constipation, vomiting, confusion, disorientation, memory impairment and hallucinations.

The present invention provides the therapeutic benefits of dopamine transport inhibitors while demonstrating low affinity for M1 cholinergic receptors. The compounds described herein, therefore, retain benztropine's clinical utility for treating disorders associated with dopamine insufficiency in the brain while demonstrating reduced anticholinergic side effects due to limited M1 cholinergic binding.

U.S. Pat. No. 5,792,775, Newman, et al., issued Aug. 11, 1998, describes the family of 4',4"-substituted 3α-(diphenylmethoxy) tropane analogs utilized in the present invention and teaches their use for the treatment of cocaine addiction and for the diagnosis and/or monitoring (but not the treatment of) neurodegenerative disorders, such as Parkinson's disease.

SUMMARY OF THE INVENTION

The present invention relates to a method for treating a condition selected from narcolepsy, attention deficit hyperactivity disorder (ADHD), conduct disorders, alcohol addiction, tobacco addiction, nicotine addiction, inhalation disorders, Parkinsonism including Parkinson's disease, female and male orgasmic disorders, female and male sexual arousal disorders, hypoactive sexual desire disorder, and disorders characterized by anxiety and/or depression, comprising administering to a patient in need of such treatment a safe and effective amount of a compound having the formula

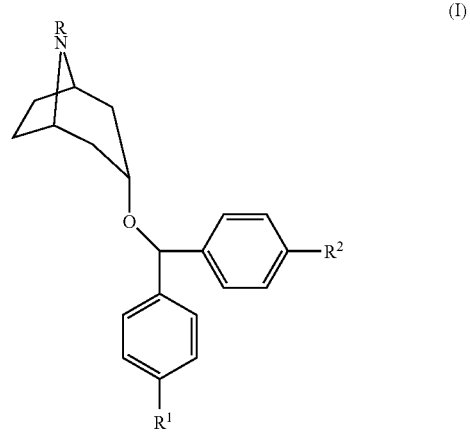

(I)

in which R is selected from hydrogen, alkyl, alkoxy, arylalkyl, aryloxyalkyl, cinnamyl and acyl; and $R^1$ and $R^2$ are independently selected from hydrogen, alkyl, alkoxy, hydroxy, halogen, cyano, amino and nitro;

with the proviso that if R is methyl, $R^1$ and $R^2$ are not both hydrogen.

A preferred compound of the formula given above is one in which R is methyl and $R^1$ and $R^2$ are both fluorine. Further, it is preferred that the compounds be administered to the patient at from about 0.05 to about 1000 mg per day (more preferably from about 0.1 to about 75 mg per day).

All percentages, proportions and ratios set forth herein are "by weight," unless otherwise specified.

All patents and publications described herein are incorporated by reference herein.

DETAILED DESCRIPTION OF THE INVENTION

The compounds used in the present invention are described in U.S. Pat. No. 5,792,775, Newman, et al., issued Aug. 11, 1998, incorporated herein by reference, as well as pharmaceutically acceptable salts of those compounds. The method of making those compounds is also described in the Newman, et al. patent. These referenced 4',4"-substituted 3α-(diphenylmethoxy) tropane analogs demonstrate high affinity for the dopamine transporter and inhibit dopamine uptake, while also exhibiting relatively limited M1 cholinergic binding. The preferred compound for use in the present invention is N-allyl-4',4"-difluoro-3α-diphenyl-methoxytropane.

The present invention relates to methods of treating specific diseases using compounds having the following formula:

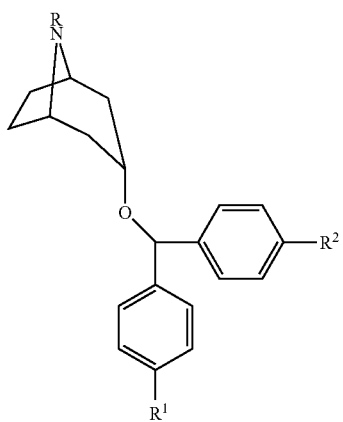

(I)

In Formula I, R is a functional group including, but not limited to, hydrogen, alkyl, alkoxy, arylalkyl, aryloxyalkyl, cinnamyl and acyl. In Formula I, $R^1$ and $R^2$ are independently selected and are functional groups including, but not limited to, hydrogen, alkyl, alkoxy, hydroxy, halogen, cyano, amino and nitro. In these compounds, when R is methyl, $R^1$ and $R^2$ cannot both be hydrogen.

The term "independently selected" is used herein to indicate that the $R^1$ and $R^2$ groups can be identical or different (e.g., $R^1$ and $R^2$ may both be methoxy, or $R^1$ may be methoxy and $R^2$ may be halogen).

The term "alkyl" is used herein to refer to a branched or unbranched, saturated or unsaturated, monovalent hydrocarbon radical containing from 1-8 carbons, cycloalkyls (3-7 carbons), cycloalkyl methyls (3-8 carbons) and arylalkyls. Suitable alkyl radicals include, for example, methyl, ethyl, n-propyl, i-propyl, 2-propenyl (or allyl), n-butyl, t-butyl, i-butyl (or 2-methylpropyl), cyclopropylmethyl, i-amyl, n-amyl, hexyl, etc. As used herein, the term "alkyl" encompasses "substituted alkyl." The term "substituted alkyl" refers to alkyls as just described above including one or more functional groups such as lower alkyl, aryl, aralkyl, acyl, halogen (i.e., haloalkyls, e.g., $CF_3$), hydroxyl, amino, acylamino, acyloxy, alkoxyl, mercapto, and the like. These groups may be attached to any carbon atom in the alkyl moiety.

The term "alkoxy" is used herein to refer to the —OR group, where R is a lower alkyl, substituted lower alkyl, aryl, substituted aryl, aralkyl, or substituted aralkyl. Suitable alkoxy radicals include, for example, methoxy, ethoxy, phenoxy, t-butoxy, etc.

The term "aryl" refers to an aromatic substituent which may be a single ring or multiple rings which are fused together, linked covalently, or linked to a common group such as an ethylene or methylene moiety. The aromatic ring(s) may include phenyl, naphthyl, biphenyl, biphenylmethyl, 2,2-diphenyl-1-ethyl, and may contain a heteroatom, such as thienyl, pyridyl and quinoxalyl. The aryl group may also be substituted with halogen atoms or other groups, such as nitro, carboxy, alkoxy, phenoxy, and the like. Additionally, the aryl group may be attached to other moieties at any position on the aryl radical which would otherwise be occupied by a hydrogen atom (such as 2-pyridyl, 3-pyridyl, and 4-pyridyl). As such, the terms "aralkyl" and "aryloxyalkyl" refer to an aryl radical attached directly to an alkyl group (e.g., 3(2-pyridyl)propyl)) or an oxygen which is attached to an alkyl group, respectively.

The term "cinnamyl" is used herein to refer to the 3-phenyl-2-propenyl radical (i.e., Ph.CH:CH.CH$_2$—). The phenyl group may be substituted with halogen atoms or other groups (e.g., nitro, hydroxy, amino, etc.).

The term "acyl" is used herein to refer to the group —C(O)R, where R is hydrogen, alkyl, substituted alkyl, aryl, or substituted aryl, as defined above.

The term "cyano" is used herein to refer to the group —CN.

The term "halogen" is used herein to refer to fluorine, bromine, chlorine, and iodine atoms.

The term "hydroxyl" is used herein to refer to the group —OH.

The term "nitro" is used herein to refer to the group —NO$_2$.

The term "amino" is used herein to refer to the group —NRR', where R and R' may independently be hydrogen, lower alkyl, substituted lower alkyl, aryl, substituted aryl or acyl.

Within the scope of Formula I, certain embodiments are preferred, namely those in which R is methyl; $R^1$ is methoxy; and $R^2$ is selected from H and methoxy. Also preferred are compounds in which R is methyl; $R^1$ is nitro; and $R^2$ is H. Also preferred are compounds in which R is methyl; $R^1$ is cyano; and $R^2$ is H. Also preferred are compounds in which R is methyl; $R^1$ is Br; and $R^2$ is selected from H, Br, Cl and F. Also preferred are compounds in which R is methyl; $R^1$ is F; and $R^2$ is selected from H, Br, F and Cl. Also preferred are compounds in which R is methyl; $R^1$ is an alkyl selected from methyl, ethyl, propyl, butyl, i-butyl, t-butyl, pentyl and hexyl; and $R^2$ is selected from H and alkyl. Also preferred are compounds in which R is methyl; $R^1$ is hydroxy; and $R^2$ is selected from H, hydroxy, Br, Cl or F. Also preferred are compounds in which R is alkyl; and $R^1$ and $R^2$ are independently selected from Br, Cl, F and I. Also preferred are compounds in which R is n-cinnamyl; and $R^1$ and $R^2$ are independently selected from Br, Cl, F and I. Also preferred are compounds in which R is arylalkyl; and $R^1$ and $R^2$ are independently selected from Br, Cl, F and I. Particularly preferred are compounds in which R is methyl and both $R^1$ and $R^2$ are fluorine atoms.

The compounds of Formula I can be prepared using the synthetic scheme set forth in the Newman, et al. patent (U.S. Pat. No. 5,792,775). Briefly, 4',4"-substituted benzhydrols are converted to benzhydrochlorides in refluxing thionyl chloride. Benzhydrochlorides are then added, neat or in a minimal volume of anhydrous diethyl ether, to tropine at 160° C., to form 4' or 4',4"-substituted 3α-(diphenylmethoxy) tropane analog 3α-(diphenylmethoxy) tropane analogs of the present invention. This second step, i.e., the melt reaction, can be carried out rapidly and without the use, or alternatively with the minimal use, of solvent.

The compounds described above are administered to a patient having a condition selected from narcolepsy, attention deficit hyperactivity disorder, conduct disorder, alcohol addiction, tobacco addiction, nicotine addiction, Parkinsonism including Parkinson's disease, female and male orgasmic disorders, female and male sexual arousal disorders, hypoactive sexual desire disorder, and disorders characterized by anxiety and/or depression. A primary focus of the present invention is the treatment of attention deficit hyperactivity disorder (ADHD) and Parkinson's disease. These are all conditions which are known to be tied in with the dopamine receptors. The compounds of the present invention not only treat those conditions, but also, because of their decreased affinity for the M1 receptor, are accompanied by minimized anticholinergic side effects. The connection between the diseases treated in the present invention and the dopamine receptors are discussed in, for example, the following references (all of which are incorporated herein by reference):

Alcohol Addiction

Eiler 2nd, et al. *D1 dopamine receptor regulates alcohol-motivated behaviors in the bed nucleus of the stria terminalis in alcohol-preferring (P) rats*. Synapse. 2003 April; 489(1):45-56.

Tupala, et al. *Dopamine receptors and transporters in the brain reward circuits of type 1 and 2 alcoholics measured with human whole hemisphere radiography*. Neuroimage. 2003 May; 19(1):145-55.

Nicotine Addiction

Bahk et al. *Dopamine D1 and D2 receptor mRNA up-regulation in the caudate-patamen and nucleus accumbens of rat brains by smoking*. Prog Neuropsycholpharmacol Biol Psychiatry. 2002 October; 26(6):1095-104.

Geracioti, et al. *Low CSF concentrations of a dopamine metabolite in tobacco smokers*. Am J. Psychiatry. 1999 January; 156(1):130-2.

Drug Addiction

Campiani, et al. *Synthesis and pharmacological evaluation of potent and highly selective D3 receptor ligands: inhibition of cocaine-seeking behavior and the role of dopamine D3/D2 receptors*. J Med Chem. 2003 Aug. 28;46(18): 3822-39.

Chartoff, et al. *Dopamine-dependent increases in phosphorylation of cAMP response element binding protein (CREB) during precipitated morphine withdrawal in primary cultures of rat striatum*. J Neurochem. 2003 October; 38(1):107-18.

O'Shea, et al. *Is frequent dosing with ecstasy a risky business of dopamine-containing neurons?* Trends Pharmacol Sci. 2003 June; 24(6):272-4.

Sexual Dysfunction (F/M Orgasmic Disorder, F/M Sexual Arousal Disorders, Hypoactive Sexual Desire Disorder)

Earle et al. *Biochemical screening in the assessment of erectile dysfunction: what tests decide future therapy?* Urology. 2003 October; 62(4):727-31.

Giuliano, et al. *Dopamine and male sexual function*. Eur Urol. 2001 December; 40(6):601-8. Review.

Sleep Disorders (Narcolepsy/Cataplexy)

Wisor et al. *Dopaminergic role in stimulant-induced wakefulness*. J Neurosci. 2001 Mar. 1;21(5):1787-94.

Honda, et al. *Dopamine D3 agonists into the substantia nigra aggravate cataplexy but do not modify sleep*. Neuroreport. 1999 Nov. 26;10(17):3713-24.

Parkinsonism Including Parkinson's Disease

Moore. *Organization of midbrain dopamine systems and the pathophysiology of Parkinson's disease*. Parkinsonism Relat Disord. 2003 August; 9 Suppl 2:S65-71. Review.

Stocchi, et al. *Dual dopamine agonist treatment in Parkinson's disease*. J Neurol. 2003 July; 250(7):822-6.

ADHD/Conduct Disorders

Young, et al. *Dopamine transporter polymorphism associated with externalizing behavior problems in children*. Am J Med Genet. 2002 Mar. 8;114(2):144-9.

Seeman, et al. *Methylphenidate elevates resting dopamine which lowers the impulse-triggered release of dopamine: a hypothesis*. Behav Brain Res. 2002 Mar. 10;130(1-2): 79-83.

Solanto. *Dopamine dysfunction in AD/HD: integrating clinical and basic neuroscience research*. Behav Brain Res. 2002 Mar. 10;130(1-2):65-71. Review Swanson et al. *Pharmacokinetic and pharmacodynamic properties of stimulants: implications for the design of new treatments for ADHD*. Behav Brain Res. 2002 Mar. 10;130(1-2):73-8. Review.

Depression/Anxiety/Stress Disorders

Wall, et al. *Infralimbic D2 receptor influences on anxiety-like behavior and active memory/attention in CD-1 mice*. Prog Neuropsychopharmacol Biol Psychiatry. 2003 May; 27(3):395-410.

Laasko, et al. *Personality traits and striatal dopamine synthesis capacity in healthy subjects*. Am J Psychiatry. 2003 May; 160(5):904-10.

Lawford, et al. *D2 dopamine receptor gene polymorphism: paroxetine and social functioning in posttraumatic stress disorder*. Eur Neuropsychopharmacol. 2003 October; 13(5):313-20.

Buller, et al. *Systemic apomorphine alters HPA axis responses to interleukin-1 beta administration but not sound stress*. Psychoneuroendocrinology. 2003 August;28 (6):715-32.

Brunswick, et al. *Greater availability of brain dopamine transporters in major depression shown by [99m Tc]TRODAT-1 SPECT imaging*. Am J Psychiatry. 2003 October; 160(10):1836-41.

Kondo, et al. *Combination of dopamine D2 receptor gene polymorphisms as a possible predictor of treatment-resistance to dopamine antagonists in schizophrenic patients*. Prog Neuropsychopharmacol Biol Psychiatry. 2003 September; 27(6):921-6.

The compounds used in the present invention may be administered by any conventional route, such as orally, transdermally, subcutaneously, parenterally, intramuscularly, intravenously, intraperitoneally, or via inhalation. Oral, parenteral and subcutaneous administration are preferred. The compounds used in the present invention may be administered alone or in combination with other therapies conventionally known for treating attention deficit hyperactivity disorder (ADHD), conduct disorder, alcohol addiction, tobacco addiction, nicotine addiction, inhalation disorders, Parkinsonism including Parkinson's disease, female and male orgasmic disorders, female and male sexual arousal disorders, hypoactive sexual desire disorder, as well as conventional therapies for treating anxiety and/or depression.

The active compounds are administered to a patient in a "safe and effective amount," i.e., an amount which provides the desired clinical benefit based on size, weight, age, physical and mental condition of the patient, and severity of the condition being treated, while minimizing any undesirable side effects. The precise dosages to be administered will be determined based on the judgment of the treating physician. Typical dosages for administration of the active compounds are from about 0.05 to about 1000 milligrams (mg) per day, more preferably from about 0.1 to about 100 mg per day, more preferably from about 0.1 to about 75 mg/day, more preferably from about 0.1 to about 50 mg/day, most preferably from about 5 to about 10 mg/day. The desired dosage may be administered in one, two or three subdoses at suitable times during the day. The subdoses may consist of 0.05 to 1000 mg per subdose, preferably 0.1 to 100 mg per subdose, most preferably 0.5 to 10 mg per subdose. The desired dosage will depend on the particular compound to be utilized, the disease to be treated, the severity of the disease, the route of administration, the weight and health of the patient, and the judgment of the treating physician. The active compound may be administered in a timed or delayed release dosage form thereby allowing treatment over an extended period of time.

For oral administration, conventional solid carriers for the active compound may be employed, such as pharmaceutical grades of cellulose, glucose, lactose, mannitol, magnesium stearate, sodium saccharin, sucrose, talcum or similar solid carriers. A pharmaceutically acceptable dosage for oral administration may be manufactured incorporating any customary nontoxic pharmaceutical excipient, such as those excipients described above, and generally about 5% to about 95% of the active compound, more preferably about 25% to 75% of the active compound.

The compounds described herein, together with a conventional pharmaceutically acceptable adjuvant, carrier or diluent, may thus be placed into the form of a pharmaceutical composition and unit dosages thereof, and in such form may be employed as solids, such as tablets or filled capsules, or liquids, such as solutions, suspensions, emulsions, elixirs or capsules filled with the same, all for oral use; in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The compounds described herein can be administered in a wide variety of oral and parenteral dosage forms. It will be obvious to those skilled in the art that the following dosage forms may comprise, as the active component, either a compound described herein or a pharmaceutically acceptable salt of such a compound.

For preparing pharmaceutical compositions of the compounds described herein, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid admixed with the finely divided active component.

In tablets, the active component is mixed with the carrier having the necessary binding capacity in suitable proportions and compacted in the shape and size desired.

The powders and tablets typically contain from about 5 or 10% to about 70% of the active compound. Suitable carriers include, for example, magnesium carbonate, magnesium stearate, talc, sugar, lactose, pectin, dextrin, starch, gelatin, tragacanth, methylcellulose, sodium carboxymethylcellulose, low melting wax, cocoa butter, and the like. The description herein is intended to include the formulation of the active compound with an encapsulating material as carrier providing a capsule in which the active compound, with or without additional carriers, is surrounded by the encapsulating material, which is thus in association with it. Similarly, cachets and lozenges are included. Tablets, powders, capsules, pills, cachets, and lozenges can be used as solid forms suitable for oral administration.

For preparing suppositories, a low melting wax, such as an admixture of fatty acid glycerides or cocoa butter, is first melted and the active material is dispersed homogeneously therein, as by stirring. The molten homogeneous mixture is then poured into convenient sized molds, allowed to cool, and thereby to solidify.

Formulations suitable for vaginal administration may be presented as pessaries, tampons, creams, gels, pastes, foams or sprays containing, in addition to the active ingredient, such carriers as are known in the art to be appropriate.

Liquid form preparations include solutions, suspensions, and emulsions, for example, water or water-propylene glycol solutions. Parenteral injection liquid preparations can be formulated as solutions in, for example, aqueous polyethylene glycol solution.

The compounds described above may be formulated for parenteral administration (e.g., by injection, for example, bolus injection or continuous infusion) and may be presented in unit dosage form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

Aqueous solutions suitable for oral use can be prepared by dissolving the active compound in water and adding suitable colorants, flavors, preservatives, stabilizing and/or thickening agents, as desired.

Aqueous suspensions suitable for oral use can be made by dispersing the finely divided active component in water with viscous material, such as natural or synthetic gums, resins, methylcellulose, sodium carboxymethylcellulose, or other well-known suspending agents.

Also included within the scope of this invention are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

For topical administration to the epidermis, the compounds described above may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oil base and will in general also contain one or more art-known emulsifying agents, stabilizing agents, dispersing agents, suspending agents, thickening agents, or coloring agents.

Formulations suitable for topical administration in the mouth include lozenges comprising active component in a flavored base, usually sucrose and acacia or tragacanth; pastilles, comprising the active component in an inert base such as gelatin or glycerin; and mouthwashes comprising the active component in a suitable liquid carrier.

Solutions or suspensions are applied directly to the nasal cavity by conventional means, for example, with a dropper, pipette or spray. The formulations may be provided in single or multidose form. In the case of a dropper or pipette, this may be achieved by the patient administering an appropriate, predetermined volume of the solution or suspension. In the case of a spray, the active component may be administered, for example, by means of a metering atomizing spray pump.

Administration to the respiratory tract may also be achieved by means of an aerosol formulation in which the active component is provided in a pressurized pack with a suitable propellant, such as a chlorofluorocarbon, for example, dichlorodifluoromethane, trichlorofluoromethane, or dichlorotetrafluoroethane, carbon dioxide, or other suitable gas. The aerosol may conveniently also contain a surfactant, such as lecithin. The dosage of drug may be controlled by provision of a metered valve.

Alternatively, for nasal administration, the active ingredient may be provided in the form of a dry powder, for example, a powder mix of the therapeutic compound in a suitable powder base, such as lactose, starch, starch derivatives such as hydroxypropylmethyl cellulose and polyvinylpyrrolidone (PVP). Conveniently, the powder carrier will form a gel in the nasal cavity. The powder composition may be presented in unit dosage form, for example, in capsules or cartridges of, e.g., gelatin, or blister packs from which the powder may be administered by means of an inhaler.

In formulations intended for administration to the respiratory tract, including intranasal formulations, the compound will generally have a small particle size, for example of the order of 5 microns or less. Such a particle size may be obtained by means known in the art, for example by micronization.

When desired, formulations adapted to give sustained release, timed release or delayed release of the active component may be employed.

The pharmaceutical preparations are preferably in unit dosage forms. In such form, the preparation is subdivided into unit doses containing appropriate quantities of the active component. The unit dosage form can be packaged, the package containing discrete quantities of preparation, such as a packeted tablet, capsule or powders in a vial or ampoule. Also, the unit dosage form can be a capsule, tablet, cachet, or lozenge itself, or it can be the appropriate number of any of these in packaged form.

Tablets or capsules for oral administration and liquids for intravenous administration are preferred pharmaceutical compositions for use in the method of the present invention.

What is claimed is:

1. A method for treating attention deficit hyperactivity disorder, comprising administering to a patient in need of such treatment a safe and effective amount of a compound having the formula:

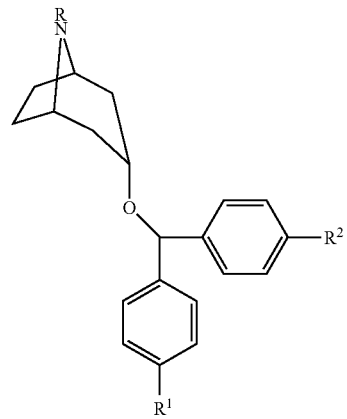

(I)

in which R is selected from hydrogen, alkyl, alkoxy, arylalkyl, aryloxyalkyl, cinnamyl, and acyl; and $R^1$ and $R^2$ are independently selected from hydrogen, alkyl, alkoxy, hydroxy, halogen, cyano, amino and nitro;

with the proviso that if R is methyl, $R^1$ and $R^2$ are not both hydrogen.

2. The method according to claim 1 wherein the compound is administered to the patient at from about 0.5 to about 1000 mg per day.

3. The method according to claim 2 wherein the compound is administered to the patient at from about 0.1 to about 100 mg per day.

4. The method according to claim 2 wherein R is methyl, and $R^1$ and $R^2$ are both fluorine.

5. The method according to claim 2 wherein R is methyl, and $R^1$ and $R^2$ are both chlorine.

6. The method according to claim 2 wherein R is alkyl, and $R^1$ and $R^2$ are selected from hydrogen and halogen.

7. The method according to claim 6 wherein $R^1$ is bromine and $R^2$ is selected from hydrogen, bromine, chlorine and fluorine.

8. The method according to claim 2 wherein the compound is administered as part of a pharmaceutical composition together with a pharmaceutically acceptable carrier.

9. The method according to claim 3 wherein R is methyl, and $R^1$ and $R^2$ are both fluorine.

10. The method according to claim 2 wherein the compound is administered to the patient orally.

11. The method according to claim 2 wherein the compound is administered to the patient together with a conventional therapy for the condition being treated.

12. The method according to claim 2 wherein the dosage is from about 5 to about 10 mg per day.

* * * * *